United States Patent [19]

Brox et al.

[11] Patent Number: 4,891,229
[45] Date of Patent: Jan. 2, 1990

[54] SOFT GELATIN CAPSULES AND PROCESSES FOR THEIR MANUFACTURE

[76] Inventors: Werner Brox, Kätchen-Paulusstrasse 6, 6124 Beerfelden; Wilfried Gabler, Neckarstaden 18, 6900 Heidelberg, both of Fed. Rep. of Germany

[21] Appl. No.: 258,114

[22] Filed: Oct. 14, 1988

Related U.S. Application Data

[63] Continuation of Ser. No. 912,585, filed as PCT EP85/00679 on Dec. 6, 1985, published as WO86/03406 on Jun. 19, 1986, abandoned.

[30] Foreign Application Priority Data

Dec. 12, 1984 [DE] Fed. Rep. of Germany ....... 3445237

[51] Int. Cl.$^4$ ............................................... A61K 9/64
[52] U.S. Cl. ................................................... 424/456
[58] Field of Search ........................ 424/451, 456, 452

[56] References Cited

U.S. PATENT DOCUMENTS 2,638,686  5/1953  Stirn et al. ............................... 34/17
4,088,750  5/1978  Creswell et al. ...................... 424/456
4,609,403  9/1986  Withwer et al. ...................... 424/456

FOREIGN PATENT DOCUMENTS 1467920  1/1969  Fed. Rep. of Germany .
1617845  3/1972  Fed. Rep. of Germany .
2507635  8/1975  Fed. Rep. of Germany .
7955     5/1970  France .

OTHER PUBLICATIONS

The Merck Index, Ninth Edition, 1976, p. 583.
"Die Kapsel", Stuttgart 1982, pp. 58–82.
"Arzneimittel-Forschung", Feb. 1956, pp. 75–77.

Primary Examiner—Thurman K. Page
Assistant Examiner—Leon R. Horne
Attorney, Agent, or Firm—Wegner & Bretschneider

[57] ABSTRACT

Soft gelatin capsules with a gelatin shell, at least one plasticizer and a capsule filling that contains at least one pharmacologically-active substance and a solvent containing at least 50% by weight of a mixture of polyethylene glycol ethers of tetrahydrofurfuryl alcohol having the formula I

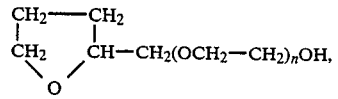

where n = 1 to 6. The capsules must be dried for 5 to 10 days in manufacture.

2 Claims, No Drawings

SOFT GELATIN CAPSULES AND PROCESSES FOR THEIR MANUFACTURE

This application is a continuation of U.S. application Ser. No. 912,585, filed as PCT SP85/00679 on Dec. 6, 1985 published as WO86/03406 on Jun. 19, 1986, now abandoned.

DESCRIPTION OF THE INVENTION

The present invention concerns soft gelatin capsules with a gelatin shell, at least one plasticizer and a capsule filling which contains at least one pharmacologically-active substance and a solvent, as well as processes for their manufacture.

Gelatin capsules, especially soft gelatin capsules, have become increasingly important as a form of medication since it became feasible, in the 1930's, to manufacture them by making and filling the capsules in one operation. Compared to other dosage forms they show a number of advantages. Thus they are odorless and tasteless, they can be taken easily and, owing to their swelling capability and water solubility, the drugs are readily liberated in the stomach. Numerous drugs which, on account of their sensitivity to oxidation and to light, their thermal stability or their hygroscopicity, may not be processed into other medicinal forms, can be encapsulated without impairment of their function.

Soft gelatin capsules serve chiefly for the containment of liquids, i.e. oily solutions, suspensions or emulsions. Vegetable, animal and mineral oils, liquid hydrocarbons, ethereal oils and also polyethylene glycols are in use as fillings. Fats and waxes are also applied or admixed to increase the consistency.

Polyethylene glycols are superior to other possible filling materials for soft gelatin capsules in a number of ways. In contrast to oily liquids, polyethylene glycols are mixable with water in all proportions.

At the same time, because polyethylene glycols are able to dissolve many drugs which are sparingly soluble or insoluble in water, the use of polyethylene glycols with such drugs makes possible a particularly favourable liberation of the active material. In many cases, sparingly water soluble drugs which have been dissolved in polyethylene glycols and then put into soft gelatin capsules are outstanding, by virtue of an exceptionally good bio-availability of the drug.

From DE-OS No. 33 07 353 of the applicant, soft gelatin capsules are known in which the dried capsule shell contains 4 to 40% by weight of sorbitol and/or sorbitan, the polyethylene glycol used in the capsule filling for solution and suspension of the active material is at least 50% by weight a polyethylene glycol having a mean molecular weight of 600, and the capsule filling contains up to 20% by weight of glycerol and/or propylene glycol. These soft gelatin capsules have been remarkably successful, yet they still have the disadvantage that a number of active materials are not sufficiently soluble in polyethylene glycol. Consequently, large capsules are necessary for the encapsulation of such sparingly soluble active materials. There exists, therefore, a continuing need for solvents which are able to dissolve larger amounts of active materials and yet can be processed into stable soft gelatin capsules. Solvents suitable for human consumption, such as ethanol, propylene glycol, dimethyl acetamide, lactic acid, glycerol, butanediol and the polyethylene glycol ether of tetrahydrofurfuryl alcohol, have been shown by the investigations of the applicant to be unsuitable for introduction into soft gelatin capsules in larger quantities, because the capsule fillings made with these solvents cause, after a short time, softening and deformation of the capsules produced, which therefore are not marketable. The reasons for these stability problems are evidently to be sought in the good water miscibility and the lower molecular weight of these solvents.

Surprisingly, it has now been found that mixtures of polyethylene glycol ethers of tetrahydrofurfurol are suitable solvents for active materials in soft gelatin capsules, if the capsule filling is encapsulated in a wet gelatin shell and the capsules obtained are intensively dried for at least 5 days, and preferably for 6 to 10 days. After 5 to 10 days, the quantities of water which pass from the wet gelatin shell into the capsule filling during encapsulation have obviously been removed to such an extent that they, together with the polyethylene glycol ethers of tetrahydrofurfuryl alcohol, are no longer able, subsequently, to soften the gelatin shell again and enable the low molecular weight solvents to escape. Such a long and intensive drying of soft gelain capsules is decidedly unusual; commonly they are dried for only 1 to 4 days. Longer drying times not only cause unnecessary costs, but also lead to an undesirable hardening and embrittlement of the capsule shell. In the inventive process, certain amounts of the polyethylene glycol ethers of tetrahydrofurfurol apparently migrate into the capsule shell an function there as a softener, counteracting the hardening and embrittlement of the capsule shell otherwise observed on drying for too long. These quantities of the polyethylene glycol ethers of tetrahydrofurfurol, functioning as a softener in the capsule shell, also lead, however, to increased sensitivity of the inventive capsules to atmospheric moisture, so the finished capsules should be stored out of contact with atmospheric moisture. However, capsules manufactured according to the invention and stored with atmospheric moisture excluded have been found to be still completely stable after 3 years. For the first time, therefore, the manufacture of stable soft gelatin capsules with a low molecular weight organic solvent, mixable with water in all proportions, has been successful and a wide field of possible new applications for this solvent has been opened up.

The polyethylene glycol ethers of tetrahydrofurfurol have the general formula I. In particular, mixtures in which n=1 to 5 or in which n=1 and 2 are commercially available and suitable for human consumption. Thus the commercial products "Glycofurol 75" (a mixture of mono- and di-ethylene glycol ethers in a ratio of approximately 1:1, with a mean molecular weight of about 168) and Tetraglykol ® (a mixture of mono-ethylene glycol ether, di-ethylene glycol ether and variable proportions of tri-, tetra-and penta-ethylene glycol ethers, with a mean molecular weight of about 190) are especially suitable. A number of sparingly soluble active materials are substantially more soluble in these solvents than in polyethylene glycol, so that soft gelatin capsules according to the invention which are substantially smaller and more pleasant to take may be manufactured. For example, the two interesting active materials, diazepam and nifedipine, are practically twice as soluble in the solvent used according to the invention as in Polyethylenglykol 400.

In addition, it has been found that not only pure mixtures of polyethylene glycol ethers of tetrahydrofurfuryl alcohol are suitable, but also mixtures with other customary solvents and solvent aids. In particular, up to 50% by weight of polyethylene glycol with a molecular weight of 300 to 600 can be added to the polyethylene glycol ethers of tetrahydrofurfuryl alcohol without changing it's solubility for sparingly soluble active materials too much. Solvent aids and emulsifiers, which are themselves soluble, can be added to increase the solubility of certain active materials in the solvents and solvent mixtures used according the the invention.

The customary plasticizers, such as glycerol, sorbitol, sorbitan etc. are added to the gelatin shell.

In addition, other customary auxiliary agents such as preservative (e.g. p-aminobenzoic acid and potassium sorbate), dyestuffs, pigments, flavourings or perfumes can be added to the capsule shell. Desirably, the finished capsules can subsequently also be provided with special coatings to facilitate or improve their application. The polyethylene glycol ethers of tetrahydrofurfuryl alcohol used according to the invention are pharmacologically and toxicologically unobjectionable and are already established to a considerable extent for the manufacture of injection solutions. In the past, the oral application of active materials in these solvents has not occurred because the polyethylene glycol ethers of tetrahydrofurfuryl alcohol taste decidedly unpleasant. A further advantage of the present invention is, therefore, that these good solvents for many active materials have now also become available for oral dosage forms. The relatively small amounts of the solvents in the capsule shell do not in any way impair the oral application of the inventive soft gelatin capsules.

The inventive soft gelatin capsules and the process for their manufacture are explained in more detail in the following examples and comparative tests.

EXAMPLE 1

500 mg of the commercial product Tetraglykol ® was first, without addition of active materials or auxiliary agents, introduced into soft gelatin capsules which were then dried at 20° C. and 20 to 25% relative humidity, some for only 1 day and some for 3, 5, 8 and 10 days. After a few weeks the solvent escaped through the capsule shell from those capsules that were dried for only 1 day, so that these capsules were useless as a commercial product. The capsules that were dried for 3 days were stable for only 12 months. The capsules that had been dried according to the invention for 5, 8 or 10 days were, under the same storage conditions, completely stable for 3 years. Also, with 8 and 10 days drying, no embrittlement took place.

EXAMPLE 2

Comparative solubility investigations of the active materials nifedipine and diazepam in Polyethylenglykol 400 and Tetraglykol ® yielded the following values, in % by weight, for the maximum solubility at 21° C.:

| Active material | Diazepam | Nifedipine |
|---|---|---|
| PEG 400 | 5.9% | 4.9% |
| Tetraglykol ® | 11.5% | 10.2% |

The following recipes were prepared, corresponding to the usual dosages of nifedipine and diazepam. The data refer to mg/capsule.

| | | |
|---|---|---|
| 1. | Nifedipine | 10.0 mg |
| | Tetraglykol ® | 110.0 mg |
| | | 120.0 mg |
| 2. | Diazepam | 5.0 mg |
| | Tetraglykol ® | 115.0 mg |
| | | 120.0 mg |
| 3. | Diazepam | 5.0 mg |
| | Tetraglykol ® | 60.0 mg |
| | PEG 400 | 50.0 mg |
| | Glycerol | 5.0 mg |
| | | 120.0 mg |

These solutions of active materials were formed into oval capsules with the very small, and therefore readily swallowed, capsule size of 2 minims and dried for 6 days in each case. On storage in the absence of atmospheric moisture the capsules were completely stable like the capsules without the active material.

What is claimed is:

1. Processes for the manufacture of soft gelatin capsules with a gelatin shell, at least one plasticizer and a capsule filling that contains at least one pharmacologically-active substance and a solvent, characterized in that at least 50% by weight of a mixture of polyethylene glycol ethers of tetrahydrofurfuryl alcohol having the formula I

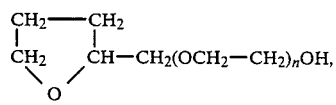

where n = 1 to 6, is used as the solvent, encapsulated in a wet gelatin shell, and that the capsules obtained are dried for 5 to 10 days.

2. Processes according to claim 1 characterized in that n = 1 to 2.